United States Patent
Lipman et al.

(10) Patent No.: US 6,875,234 B2
(45) Date of Patent: Apr. 5, 2005

(54) DUAL-RADIUS GLENOID PROSTHETIC COMPONENT FOR TOTAL SHOULDER ARTHROPLASTY

(75) Inventors: Joseph Lipman, New York, NY (US); William O. Thompson, Wappinger Falls, NY (US); Russell F. Warren, Greenwich, CT (US)

(73) Assignee: The New York, Society for the Ruptured and crippled Maintaining Hospital for Special Surgery, New York, NY (US)

(*) Notice: Subject to any disclaimer, the term of this patent is extended or adjusted under 35 U.S.C. 154(b) by 0 days.

(21) Appl. No.: 10/682,836

(22) Filed: Oct. 8, 2003

(65) Prior Publication Data

US 2004/0122520 A1 Jun. 24, 2004

Related U.S. Application Data

(63) Continuation of application No. PCT/US02/05073, filed on Feb. 21, 2002.
(60) Provisional application No. 60/269,821, filed on Feb. 21, 2001.

(51) Int. Cl.$^7$ .................................................. A61F 2/40
(52) U.S. Cl. .................................................. 623/19.12
(58) Field of Search ............................ 623/19.11–19.16

(56) References Cited

U.S. PATENT DOCUMENTS

| 5,723,018 A | * | 3/1998 | Cyprien et al. | 623/19.13 |
| 5,928,285 A | * | 7/1999 | Bigliani et al. | 623/19.13 |

* cited by examiner

*Primary Examiner*—Eduardo C. Robert
*Assistant Examiner*—Michael B. Priddy
(74) *Attorney, Agent, or Firm*—Darby & Darby

(57) ABSTRACT

A dual-radius glenoid component of a shoulder joint prosthesis for use in total shoulder arthroplasty has two radii of curvature. At substantially the center of the articulating surface a first non-conforming radius of curvature is provided, while a second conforming radius of curvature, smaller than that of the first radius of curvature and more closely conforming to the curvature of the humeral component, is disposed about the periphery of the articulating surface. The central non-conforming radius of curvature provides reduced constraint of the humeral component. In contrast, the conforming peripheral radius of curvature provides maximum constraint of the humeral component. When the humeral component is substantially centered on the articulating surface reduced constraint is placed on the prosthesis and less load is transferred to the bone-implant interface. As the humeral component translates towards the periphery, constraint on the prosthesis increases to prevent dislocation.

12 Claims, 4 Drawing Sheets

DUAL-RADIUS GLENOID PROSTHETIC COMPONENT FOR TOTAL SHOULDER ARTHROPLASTY

CROSS-REFERENCE TO RELATED APPLICATIONS

This application is a cotinuation of PCT/U.S. 02/05073 filed Feb. 21, 2002, which claims the benefit of U.S. Provisional Application No. 60/269,821, filed on Feb. 21, 2001, which is herein incorporated by reference in its entirety.

FIELD OF THE INVENTION

The present invention relates to total shoulder arthroplasty, and more particularly, to a dual-radius glenoid prosthetic component of a prosthetic shoulder joint.

DESCRIPTION OF RELATED ART

Approximately 20,000 total shoulder arthroplasties are performed each year in the United States. During the total shoulder arthroplasty operation, the humeral head and glenoid of the shoulder are resurfaced and a cavity is created in the intramedullary canal of the humerus. The resurfaced humerus and glenoid are then fitted with respective humeral and glenoid prosthetic components. An articulating surface is defined along the portion of the glenoid component that engages and articulates with the head portion of the humeral component. The humeral component is typically a cobalt-chrome sphere that replaces a portion of the humeral head, articulates with respect to the glenoid component, and includes a stem that is received in the cavity created in the intramedullary canal of the humerus to augment fixation. The shoulder joint prosthetic components may be affixed to the resurfaced humerus and glenoid using an adhesive, for example, polymethyl methacrylate (PMMA), or mechanically such as by screws or press-fit into place. The glenoid component is preferably an ultra-high molecular weight polyethylene (UHMWPE) bearing that may be metal-backed and is affixed in place using adhesive or mechanical means.

Over the years, different schools of thought have been pursued with regard to the amount of constraint desired between the components of the shoulder joint prosthesis assembly. A first approach is to design the articulating surface of the glenoid component 100 so that its articulating surface 105 has a single radius of curvature that does not conform in shape (non-conforming and less constrained) to that of the humeral component 110, as shown in FIG. 1a–d. FIG. 1a is a perspective view of a prior art glenoid component 100 in which the articulating surface 105 has a spherical radius of curvature R1, for example, of 1.5 inches. A top view of the conventional humeral and glenoid components is shown in FIG. 1b. As shown in the cross-sectional views of FIGS. 1c and 1d, the radius of curvature of the articulating surface 105 of the glenoid component 100 is not the same (non-conforming) as that of the humeral component 110. A glenoid component with a non-conforming articulating surface produces less constraint than a glenoid component having a conforming articulating surface. The underlying principle behind this design is that non-conforming surfaces more closely mimic natural shoulder kinematics wherein the humerus tends to translate along the surface of the glenoid and rotate about the humeral head center.

In contrast, another conventional approach is to design the surfaces between the glenoid and humeral components to be conforming (fully constrained), as shown in FIGS. 2a–d. In FIG. 2a the articulating surface 205 of the glenoid component 200 has a spherical radius of curvature R2, for example, of 1.0 inches, that conforms to the radius of curvature of the humeral component 210, as shown in the cross-sectional views of FIGS. 2c and 2d. A conforming articulating surface reduces contact stress between the two engaging surfaces thereby producing less wear and tear on the prosthetic components. Furthermore, conforming surfaces are more resistant to dislocation.

Nonetheless, problems arise with both of these conventional designs. Cross-sectional views of the conforming design with small displacement and large displacement of the humeral component relative to the glenoid component are shown in FIGS. 3a and 3b, respectively. In the fully constrained (conforming) design, the humeral component 210 rides up the rim of the glenoid component 200 as translation increases. This motion increases the torque applied to the bone/implant interface, which may lead to a greater incidence of loosening of the prosthesis components. Glenoid component loosening is the leading complication of total shoulder arthroplasty.

On the other hand, the increased radius of curvature of the glenoid component in the non-conforming design reduces the ability of the glenoid component to withstand lateral forces. Also, the non-conforming design is less stable in that during translation of the joint only a small amount of soft tissue displacement is necessary to cause dislocation, as shown in FIG. 4b. Instability, is the second highest complication of total shoulder arthroplasty.

It is therefore desirable to develop a shoulder prosthesis assembly that combines the advantages associated with each of the convention designs without the problems arising from each.

SUMMARY OF THE INVENTION

The present invention is directed to a shoulder prosthesis comprising a glenoid component and a humeral component, wherein the articulating surface of the glenoid component that mates with the humeral component has two radii of curvature. A first radius of curvature at substantially the center of the articulating surface, where it is desirable to minimize constraint, is larger than a second radius of curvature at the periphery to more closely mimic the radius of the humeral component. In this way, as the humeral head moves towards the periphery, the constraint on the articulating surfaces increases, as needed. While the joint is substantially centered, minimal constraint is exhibited thereby reducing the load transferred to the bone-implant interface. Accordingly, the structure requires substantially greater force to dislocate than conventional non-conforming devices, while providing substantially similar constraint to that of the conventional non-conforming device for relatively small translations.

In some respects the structure in accordance with the present invention more closely mimics the natural kinematics of shoulder movement in which the glenoid is surrounded by a soft-tissue ring of fibrous cartilage called the labrum that helps to constrain the joint.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

FIGS. 5a–5d show an exemplary embodiment of a dual-radius glenoid component 500 in accordance with the present invention that forms part of a shoulder joint prosthesis used during total shoulder arthroplasty. Glenoid component 500 has an articulating surface 505 formed by two radii of curvature. A first, central or inner area 507 has a first radius of curvature. Surrounding the first, central or inner area 507 is a second, peripheral or outer area 506 defined by a second radius of curvature. The second radius of curvature substantially conforms with the radius of curvature of the humeral component, while the first radius of curvature does not. In addition, the first radius of curvature is greater than the second radius of curvature. In a preferred embodiment, the second radius of curvature is approximately equal to the radius of curvature of the humeral head component at approximately 1.0 inch, the first radius of curvature is between approximately 1.1 inches and approximately 1.5 inches, and the second curvature is substantially tangent to the periphery of the first curvature. By way of example, the dual-radius glenoid component shown in FIG. 5a has a first radius of curvature of approximately 1.5 inches and a second radius of curvature of approximately 1.0 inches (equal to the radius of curvature of the humeral component). These first and second radii of curvature values of the glenoid component are by way of example only and are not intended to limit the scope of the invention.

Figure 1A:
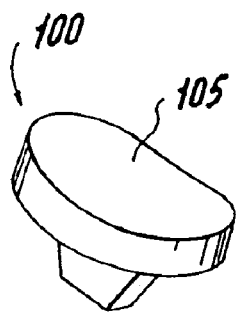
FIG. 1a is a perspective view of a prior art non-conforming glenoid component.
Figure 1B:
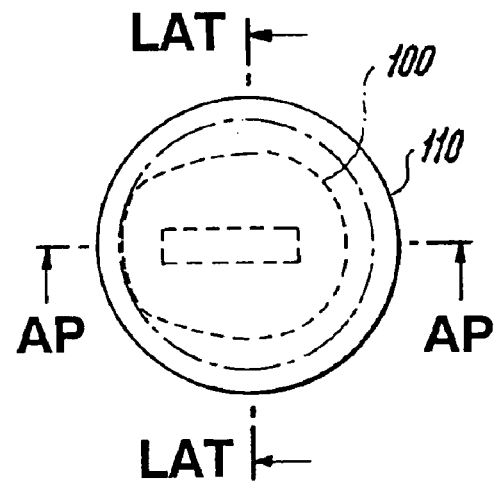
FIG. 1b is a top elevational view of the glenoid component in FIG. 1a and the humeral component.
Figure 1C:
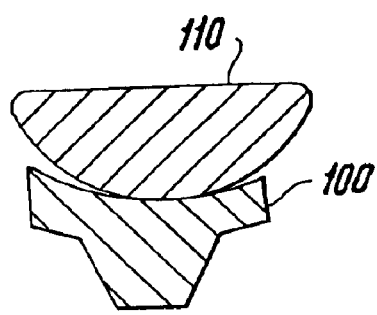
FIG. 1c is a cross-sectional view along lines AP-AP of the glenoid component in FIG. 1b with respect to the humeral component.
Figure 1D:
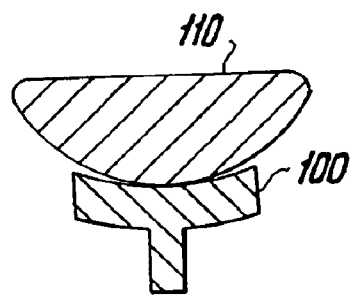
FIG. 1d is a cross-sectional view along lines LAT-LAT of the glenoid component in FIG. 1b with respect to the humeral component.
Figure 2A:
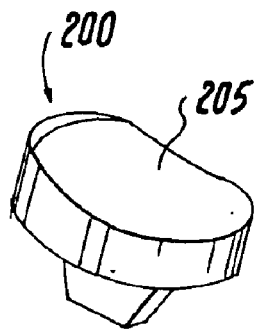
FIG. 2a is a perspective view of a prior art conforming glenoid component.
Figure 2B:
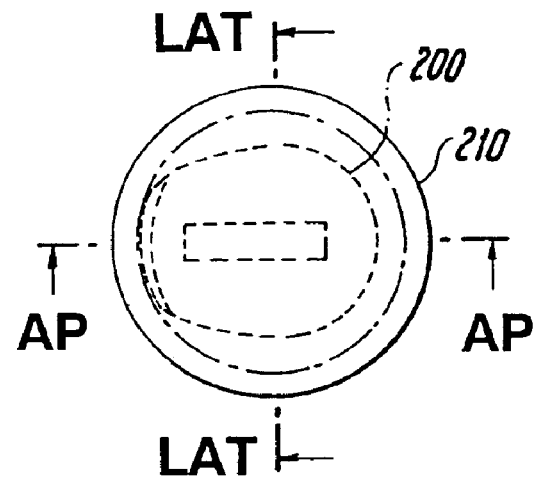
FIG. 2b is a top elevational view of the glenoid component in FIG. 2a and the humeral component.
Figure 2C:
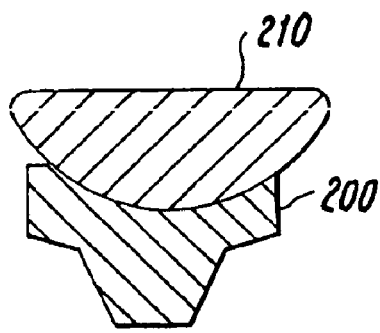
FIG. 2c is a cross-sectional view along lines AP-AP of the glenoid component in FIG. 2b with respect to the humeral component.
Figure 2D:
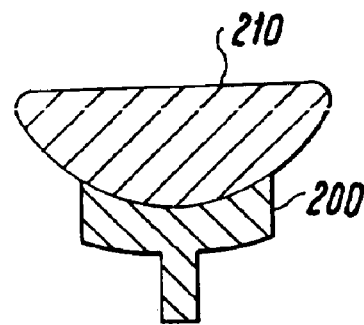
FIG. 2d is a cross-sectional view along lines LAT-LAT of the glenoid component in FIG. 2b with respect to the humeral component.
Figure 3A:
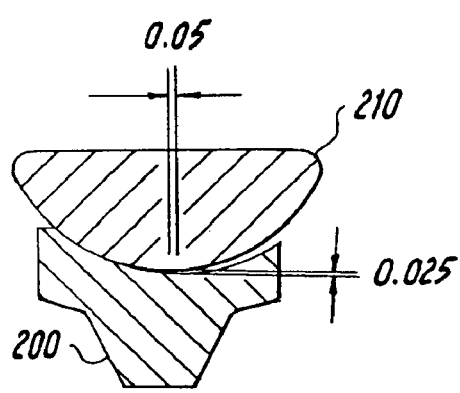
FIG. 3a is a cross-sectional view along lines AP-AP of the conforming glenoid component in FIG. 2b while substantially centered with respect to the humeral component.
Figure 3B:
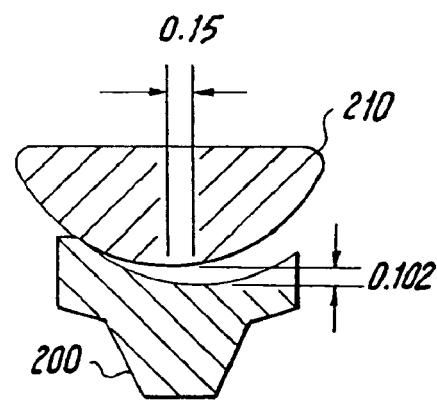
FIG. 3b is a cross-sectional view along lines AP-AP of the conforming glenoid component in FIG. 2b translated with respect to the humeral component.
Figure 4A:
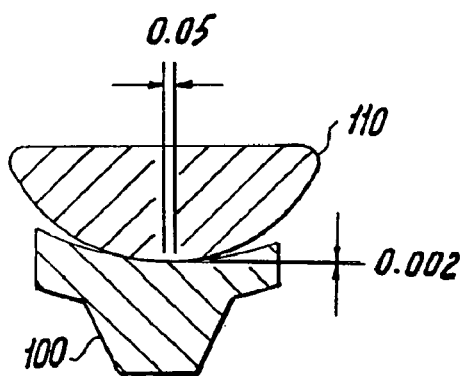
FIG. 4a is a cross-sectional view along lines AP-AP of the non-conforming glenoid component in FIG. 1b while substantially centered with respect to the humeral component.
Figure 4B:
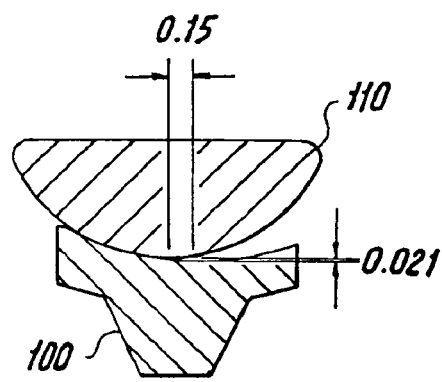
FIG. 4b is a cross-sectional view along lines AP-AP of the non-conforming glenoid component in FIG. 1b translated with respect to the humeral component.
Figure 5A:
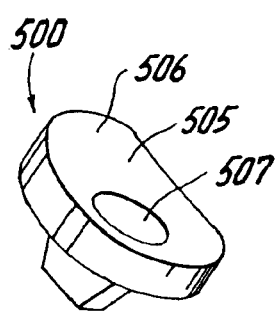
FIG. 5a is a perspective view of an exemplary dual-radius glenoid component in accordance with the present invention.
Figure 5B:
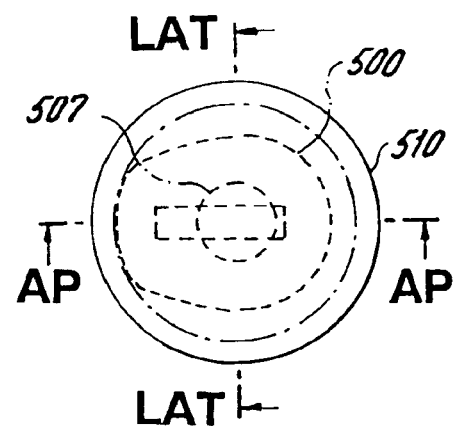
FIG. 5b is a top elevational view of the glenoid component in FIG. 5a and the humeral component.
Figure 5C:
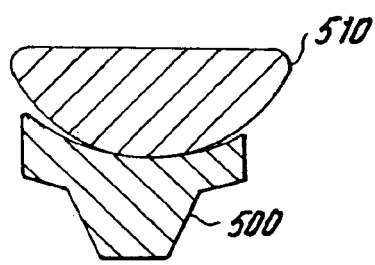
FIG. 5c is a cross-sectional view along lines AP-AP of the glenoid component in FIG. 5b with respect to the humeral component.
Figure 5D:
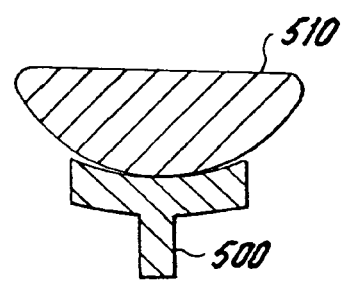
FIG. 5d is a cross-sectional view along lines LAT-LAT of the glenoid component in FIG. 5b with respect to the humeral component.
Figure 6A:
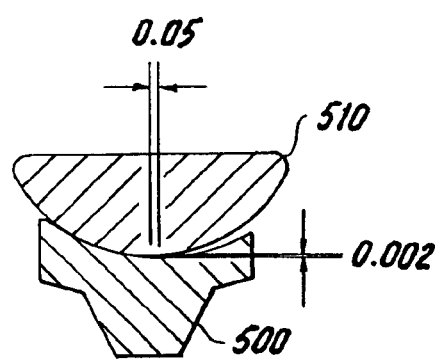
FIG. 6a is a cross-sectional view along lines AP-AP of the dual-radius glenoid component in FIG. 5b while substantially centered with respect to the humeral component.
Figure 6B:
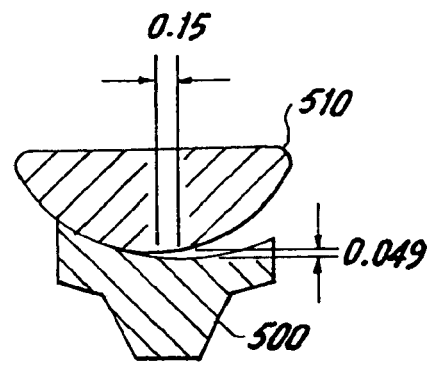
FIG. 6b is a cross-sectional view along lines AP-AP of the dual-radius glenoid component in FIG. 5b translated with respect to the humeral component.

Translational displacement of the humeral component with respect to the dual-radius glenoid component in accordance with the present invention is depicted in FIGS. 6a and 6b. A comparison of the humeral component relative to the non-conforming (FIGS. 3a and 3b), conforming (FIGS. 4a and 4b) and dual-radius (FIGS. 6a and 6b) glenoid component designs shows that the dual-radius glenoid component configuration combines the advantages of the conforming and non-conforming designs. In the example shown in FIGS. 6a and 6b, during relatively small translation (FIG. 6a) the dual-radius glenoid component exhibits minimal horizontal displacement of 0.002 inch, the same as that of the non-conforming design. Extreme translation (FIG. 6b) causes the humeral component to ride up only 0.049 inch on the rim of the dual-radius glenoid component as compared to the 0.102 inch horizontal displacement with the conforming design.

Thus, the dual-radius glenoid component design varies the constraint on the humeral component as the degree of translation increases. Minimal constraint and thus less load is transferred to the bone-implant interface while the humeral component is substantially centered relative to the glenoid component. As the degree of translation of the humeral component increases so does the constraint imposed on the humeral component thereby making the device more stable while simultaneously preventing dislocation.

The increased radius of curvature of the glenoid component in the conventional non-conforming design reduces the ability of the glenoid component to withstand lateral forces. However, the dual-radius glenoid component design is able to withstand lateral forces significantly greater than those with the non-conforming design. Table I below substantiates these findings by summarizing the results of the three different glenoid component designs to withstand lateral forces for an exemplary glenoid component having a single radius of curvature of 1.0 inch (conforming design), a single radius of curvature of 1.5 inches (non-conforming design), and a first radius of curvature of 1.5 inches and a second radius of curvature of 1.0 inch (dual-radius design).

TABLE I

Loading Capabilities for the Different Glenoid Design Types (normalized to anterior loading on the non-conforming geometry)

| Glenoid Design Type | Anterior Loading | Distal Loading | Proximal Loading |
| --- | --- | --- | --- |
| Non-Conforming | 1.00 | 1.07 | 1.39 |
| Conforming | 1.76 | 1.91 | 2.36 |
| Dual-Radius | 1.20 | 1.30 | 1.88 |

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

What is claimed is:

1. A dual-radius glenoid component of a shoulder joint for use in total shoulder arthroplasty, said glenoid component comprising:

an articulating surface including a first area and a second area, the first area being defined by a first curvature having a first radius of curvature and the second area being defined by a second curvature having a second radius of curvature, the first radius of curvature being greater than the second radius of curvature, the second area at least partially surrounding the first area.

2. The dual-radius glenoid component in accordance with claim 1, wherein the first area is substantially centered on the articulating surface and the second area is peripheral to and completely surrounds the first area.

3. The dual-radius glenoid component in accordance with claim 1, wherein the shoulder joint further includes a humeral component having a third radius of curvature, the second radius of curvature being substantially equal to the third radius of curvature.

4. The dual-radius glenoid component in accordance with claim 1, wherein the first radius of curvature is between approximately 1.1 inches and approximately 1.5 inches and the second radius of curvature is approximately 1.0 inch.

5. The dual-radius glenoid component in accordance with claim 4, wherein the first radius of curvature is approximately 1.5 inches and the second radius of curvature is approximately 1.0 inch.

6. The dual-radius glenoid component in accordance with claim 1, wherein the second curvature is tangent to the periphery of the first curvature.

7. A shoulder joint prosthesis for use in total shoulder arthroplasty comprising:

a humeral component including a head defined by a humeral component radius of curvature; and a dual-radius glenoid component having an articulating surface that engages with the head of the humeral component, the articulating surface including a first area and a second area, the first area being defined by a first curvature having a first radius of curvature and the second area being defined by a second curvature having a second radius of curvature, the first radius of curvature being greater than the second radius of curvature, the second area at least partially surrounds the first area.

8. The shoulder joint prosthesis in accordance with claim 7, wherein the first area is substantially centered on the articulating surface and the second area is peripheral to and completely surrounds the first area.

9. The shoulder joint prosthesis in accordance with claim 7, wherein the second radius of curvature is substantially equal to the radius of curvature of the humeral component.

10. The shoulder joint prosthesis in accordance with claim 7, wherein the first radius of curvature is between approximately 1.1 inches and approximately 1.5 inches, and the second radius of curvature is approximately 1.0 inch.

11. The shoulder joint prosthesis in accordance with claim 10, wherein the first radius of curvature is approximately 1.5 inches and the second radius of curvature is approximately 1.0 inch.

12. The shoulder joint prosthesis in accordance with claim 7, wherein the second curvature is tangent to the periphery of the first curvature.

* * * * *